US012746193B2

(12) United States Patent
Yamaguchi

(10) Patent No.: US 12,746,193 B2
(45) Date of Patent: Sep. 29, 2026

(54) COSMETIC COMPOSITION

(71) Applicant: AJINOMOTO CO., INC., Tokyo (JP)

(72) Inventor: Eriko Yamaguchi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 340 days.

(21) Appl. No.: 18/393,991

(22) Filed: Dec. 22, 2023

(65) Prior Publication Data

US 2024/0122841 A1 Apr. 18, 2024

Related U.S. Application Data

(63) Continuation of application No. PCT/JP2022/024958, filed on Jun. 22, 2022.

(30) Foreign Application Priority Data

Jun. 23, 2021 (JP) ................................ 2021-104443

(51) Int. Cl.

| | |
|---|---|
| ***A61K 8/88*** | (2006.01) |
| ***A61K 8/34*** | (2006.01) |
| ***A61K 8/365*** | (2006.01) |
| ***A61K 8/44*** | (2006.01) |
| ***A61K 8/49*** | (2006.01) |
| ***A61Q 19/00*** | (2006.01) |

(52) U.S. Cl.

CPC ................ *A61K 8/88* (2013.01); *A61K 8/345* (2013.01); *A61K 8/365* (2013.01); *A61K 8/44* (2013.01); *A61K 8/492* (2013.01); *A61Q 19/00* (2013.01)

(58) Field of Classification Search

None

See application file for complete search history.

(56) References Cited

U.S. PATENT DOCUMENTS

| | | | |
|---|---|---|---|
| 2014/0271510 | A1 | 9/2014 | Takino et al. |
| 2017/0181947 | A1 | 6/2017 | Haraya et al. |
| 2020/0261330 | A1 | 8/2020 | Ogino |
| 2023/0233423 | A1 | 7/2023 | Yamaguchi |

FOREIGN PATENT DOCUMENTS

| | | | |
|---|---|---|---|
| CN | 111991261 | A | 11/2020 |
| JP | 6-157237 | A | 6/1994 |
| JP | 7-277916 | A | 10/1995 |
| JP | 8-193020 | A | 7/1996 |
| JP | 2020-132619 | A | 8/2020 |
| WO | WO 2016/039407 | A1 | 3/2016 |

OTHER PUBLICATIONS

International Search Report issued Aug. 23, 2022 in PCT/JP2022/024958, 2 pages.

Ajinomoto Healthy Supply, "Deep Harmonize Emulsion", Mintel, Apr. 2010, 3 pages.

Extended European Search Report issued May 26, 2025 in European Patent Application No. 22828470.9, 10 pages.

*Primary Examiner* — Brian J Davis

(74) *Attorney, Agent, or Firm* — Oblon, McClelland, Maier & Neustadt, L.L.P.

(57) ABSTRACT

Compositions for cosmetics, containing (A) at least one polyaspartic acid or a salt thereof, (B) zinc pyrrolidonecarboxylate, and (C) at least one aliphatic hydroxycarboxylic acid having 1 to 10 carbon atoms or a salt thereof are useful as premixed compositions used for blending polyaspartic acid or a salt thereof and zinc pyrrolidonecarboxylate stably and conveniently in cosmetic compositions.

10 Claims, No Drawings

COSMETIC COMPOSITION

CROSS REFERENCES TO RELATED APPLICATIONS

This application is a continuation of International Patent Application No. PCT/JP2022/024958, filed on Jun. 22, 2022, and claims priority to Japanese Patent Application No. 2021-104443, filed on Jun. 23, 2021, both of which are incorporated herein by reference in their entireties.

BACKGROUND OF THE INVENTION

Field of the Invention

The present invention relates to compositions for cosmetics that are useful as premixed compositions capable of blending in cosmetics stably and conveniently.

Discussion of the Background

Moisturizers blended in cosmetics are required to have moisturizing power and hygroscopic capacity. Polyaspartate has been proposed as a humectant that has both such moisturizing power and hygroscopic capacity, shows good feeling of use when applied, and is highly safe (see JP-A-6-157237, which is incorporated herein by reference in its entirety).

However, since polyaspartate is an electrolyte polymer with strong cohesive property, it is difficult to stably blend polyaspartate in an emulsion composition, and peptide bonds are cleaved under acidic conditions to cause a decrease in the molecular weight. These limit the use and the amount of polyaspartate to be blended.

Zinc pyrrolidonecarboxylate, which has been reported to have sebum suppressive effect, antibacterial action, skin astringent effect, antiaging effect, and the like, is a useful cosmetic material that is widely used in skin external preparations and hair cosmetics for various applications (see WO 2016/039407, which is incorporated herein by reference in its entirety).

However, when attempts are made to blend polyaspartic acid or a salt thereof in cosmetics together with zinc pyrrolidonecarboxylate in order to impart high skin adhesion and moisture retaining property in addition to the above-mentioned effects provided by zinc pyrrolidonecarboxylate, these are not dissolved stably, resulting in a problem that a homogeneous composition cannot be obtained.

Accordingly, there is a demand for a premixed composition used for blending polyaspartic acid or a salt thereof and zinc pyrrolidonecarboxylate stably and conveniently in cosmetic compositions.

SUMMARY OF THE INVENTION

Thus, it is an object of the present invention to provide compositions for cosmetics that are useful as premixed compositions used for blending polyaspartic acid or a salt thereof and zinc pyrrolidonecarboxylate stably and conveniently in cosmetic compositions.

This and other objects, which will become apparent during the following detailed description, have been achieved by the present inventor's discovery that compositions containing (A) polyaspartic acid or a salt thereof, (B) zinc pyrrolidonecarboxylate, and (C) aliphatic hydroxycarboxylic acid having 1 to 10 carbon atoms or a salt thereof can suppress a decrease in the molecular weight of the aforementioned component (A), are stable compositions superior in the stability of component (A) and component (B) in a solution state, and can be stably and conveniently blended in cosmetics, which resulted in the completion of the present invention.

That is, the present invention provides the following.

(1) A composition for cosmetics, comprising (A) polyaspartic acid or a salt thereof, (B) zinc pyrrolidonecarboxylate, and (C) aliphatic hydroxycarboxylic acid having 1 to 10 carbon atoms or a salt thereof.

(2) The composition of (1), wherein a content of the (A) polyaspartic acid or a salt thereof is 2.5 mass % to 13 mass % as a content converted to that of a free form thereof.

(3) The composition of (1) or (2), wherein a content of the (B) zinc pyrrolidonecarboxylate is 1 mass % to 12 mass %.

(4) The composition of any of (1) to (3), wherein the (C) aliphatic hydroxycarboxylic acid having 1 to 10 carbon atoms or a salt thereof is an acyclic hydroxycarboxylic acid having 2 to 6 carbon atoms or a salt thereof.

(5) The composition of any of (1) to (4), wherein a ratio of a content of component (B) ($W_B$) to a content of component (A) ($W_A$) ($W_B/W_A$) is less than 2.4.

(6) The composition of any of (1) to (5), wherein a ratio of a content of component (B) ($W_B$) to a content of component (C) ($W_C$) ($W_B/W_C$) is less than 3.3.

(7) The composition of any of (1) to (6), further comprising (D) pyrrolidonecarboxylic acid or an alkali metal salt thereof.

(8) The composition of any of (1) to (7), further comprising (E) arginine or a salt thereof.

(9) The composition of any of (1) to (8), further comprising (F) one or more kinds selected from the group consisting of acidic amino acid and a salt thereof, basic amino acid other than arginine and a salt thereof, and neutral amino acid and a salt thereof.

(10) The composition of any of (1) to (9), further comprising one or more kinds of polyhydric alcohol.

(11) The composition of any of (1) to (10), further comprising trimethylglycine.

(12) The composition of any of (1) to (11), wherein the composition has pH 7 to 13 at 25° C.

(13) The composition of any of (1) to (12), wherein the composition is added to cosmetics containing a powder.

(14) A cosmetic comprising the composition of any of (1) to (12) and a powder.

(15) A cosmetic comprising (A) polyaspartic acid or a salt thereof, (B) zinc pyrrolidonecarboxylate, and (C) aliphatic hydroxycarboxylic acid having 1 to 10 carbon atoms or a salt thereof, and a powder.

(16) The composition of (1), wherein a content of the (A) polyaspartic acid or a salt thereof is 2 mass % to 20 mass % as a content converted to that of a free form thereof.

(17) The composition of (1) or (2), wherein a content of the (B) zinc pyrrolidonecarboxylate is 1 mass % to 15 mass %.

(18) A cosmetic comprising the composition of any of (1) to (12).

(19) A cosmetic comprising the composition of (16) or (17).

Advantageous Effects of Invention

According to the present invention, compositions for cosmetics, containing polyaspartic acid or a salt thereof and zinc pyrrolidonecarboxylate, and superior in the stability thereof can be provided.

In the composition for cosmetics of the present invention, a decrease in the molecular weight of polyaspartic acid or a salt thereof is suppressed, and further, the stability of polyaspartic acid or a salt thereof and zinc pyrrolidonecarboxylate in a solution state is improved. Therefore, the composition for cosmetics of the present invention is useful as a premixed composition for cosmetics that can be stably and conveniently blended in cosmetics, and can impart the cosmetics with high moisture retaining property and good skin adhesion, as well as sebum suppressive effect, antibacterial action, skin astringent effect, antiaging effect, and the like.

DETAILED DESCRIPTION OF THE PREFERRED EMBODIMENTS

The composition for cosmetics of the present invention contains (A) polyaspartic acid or a salt thereof, (B) zinc pyrrolidonecarboxylate, and (C) aliphatic hydroxycarboxylic acid having 1 to 10 carbon atoms or a salt thereof.

The polyaspartic acid contained as component (A) in the composition for cosmetics of the present invention is L-aspartic acid, D-aspartic acid or DL-aspartic acid polymerized by an α-amide bond or a β-amide bond.

For the purpose of the present invention, poly L-aspartic acid and poly DL-aspartic acid are preferably used, and poly L-aspartic acid is more preferably used. In addition, any of an α-amide conjugate, a β-amide conjugate, and a mixture of an α-amide conjugate and a β-amide conjugate can be used, and an α-amide conjugate and a mixture of an α-amide conjugate and a β-amide conjugate are preferably used.

In the present invention, polyaspartic acid with a weight average molecular weight of 1,000 to 100,000 as measured by gel filtration chromatography is used. Polyaspartic acid with the aforementioned weight average molecular weight of 2,000 to 50,000 is preferred, 2,000 to 10,000 is more preferred, and 3,000 to 5,000 is further preferred.

In the present invention, a salt of the above-mentioned polyaspartic acid can also be used as component (A).

The salt of polyaspartic acid is not particularly limited as long as it is a pharmaceutically acceptable salt and used for skin compositions. Examples thereof include salts with inorganic bases such as alkali metal salts (e.g., lithium salt, sodium salt, potassium salt, and the like); alkaline earth metal salts (e.g., magnesium salt, calcium salt, and the like); ammonium salt; and the like, and salts with organic bases such as alkanol amine salts (e.g., mono ethanolamine salt, diethanolamine salt, triethanolamine salt, and the like); salts with basic amino acids (e.g., arginine salt, lysine salt, histidine salt, and the like); and the like, and alkali metal salts such as sodium salt and the like are preferably used.

Polyaspartic acid or a salt thereof can be produced by a known method.

For example, a mixture of an α-amide conjugate and a (3-amide conjugate can be obtained by a solid state polymerization method including directly heating and condensing amino acid (see The Journal of the American Chemical Society 82, 3745 (1960), which is incorporated herein by reference in its entirety, etc.).

An α-amide conjugate can be obtained by a method of ring opening the N-carboxy acid anhydride of an amino acid and subjecting same to decarboxylation polymerization (see Journal of Polymer Science A14 2065 (1976) and JP-A-s46-27828, which are incorporated herein by reference in their entireties, etc.), a method of polymerizing an active amino acid ester (see JP-A-s54-47799, which is incorporated herein by reference in its entirety), a method of thermally polymerizing an N-dithiocarbonylalkoxycarbonylamino acid (see JP-B-45-9391, which is incorporated herein by reference in its entirety), and the like.

In addition, a polymer that retains the optical activity of aspartic acid used as a starting material can be obtained by ring-opening polymerization of N-carboxylic anhydride of amino acid.

In the present invention, polyaspartic acid or a salt thereof may be produced and used by the above-mentioned known methods. Alternatively, commercially available products provided by Ajinomoto Co., Inc., etc. can also be used.

In the composition for cosmetics of the present invention, one kind of the above-mentioned polyaspartic acid or a salt thereof may be used alone, or two or more kinds thereof may be selected and used in combination.

The content ($W_A$) of component (A) in the composition for cosmetics of the present invention is preferably not less than 2.5 mass %, more preferably not less than 3 mass %. In addition, the content ($W_A$) of component (A) in the composition for cosmetics of the present invention is preferably not more than 13 mass %, more preferably not more than 10 mass %.

In another embodiment of the present invention, the content ($W_A$) of component (A) in the composition for cosmetics of the present invention is preferably not less than 2 mass %, more preferably not less than 3 mass %, further preferably not less than 4 mass %, further more preferably not less than 6 mass %, particularly preferably not less than 8 mass %. In addition, the content ($W_A$) of component (A) in the composition for cosmetics of the present invention is preferably not more than 20 mass %, more preferably not more than 15 mass %, further preferably not more than 13 mass %, further more preferably not more than 11 mass %, particularly preferably not more than 10 mass %.

In still another embodiment of the present invention, the content ($W_A$) of component (A) in the composition for cosmetics of the present invention may be preferably 2 mass % to 20 mass %, more preferably 2 mass % to 15 mass %, further preferably 3 mass % to 13 mass %, further more preferably 4 mass % to 13 mass %, even more preferably 6 mass % to 13 mass %, still even more preferably 8 mass % to 13 mass %, 8 mass % to 11 mass % or 8 mass % to 10 mass %.

When a polyaspartic acid salt is contained as component (A), the above-mentioned content is shown as a content converted to that of a free form.

Zinc pyrrolidonecarboxylate contained as component (B) in the composition for cosmetics of the present invention is a zinc salt of 2-pyrrolidone-5-carboxylic acid, and any of the D-form, L-form, and DL-form can be used. L-form and DL-form are preferably used, and L-form is more preferably used. One kind of these may be used alone, or two or more kinds thereof may be used in a mixture. When a DL-form is used, the ratio of the D-form and L-form is not particularly limited.

Zinc pyrrolidonecarboxylate to be used may be produced by chemical synthesis method, enzyme method, or gene recombinant method. Alternatively, commercially available products provided by each company can also be used.

The content ($W_B$) of component (B) in the composition for cosmetics of the present invention is preferably not less than 1 mass %, more preferably not less than 3 mass %. In addition, the content ($W_B$) of component (B) in the composition for cosmetics of the present invention is preferably not more than 12 mass %, more preferably not more than 10 mass %.

In another embodiment of the present invention, the content ($W_B$) of component (B) in the composition for cosmetics of the present invention is preferably not less than 1 mass %, more preferably not less than 2 mass %, further preferably not less than 3 mass %, further more preferably not less than 4 mass %. In addition, the content ($W_B$) of component (B) in the composition for cosmetics of the present invention is preferably not more than 15 mass %, more preferably not more than 13 mass %, further preferably not more than 12 mass %, further more preferably not more than 10 mass %.

In still another embodiment of the present invention, the content ($W_B$) of component (B) in the composition for cosmetics of the present invention is preferably 1 mass % to 15 mass %, more preferably 2 mass % to 13 mass %, further preferably 3 mass % to 12 mass %, further more preferably 4 mass % to 10 mass %.

In the composition for cosmetics of the present invention, the aliphatic hydroxycarboxylic acid having 1 to 10 carbon atoms that may be contained as component (C) is an acyclic or cyclic carboxylic acid having 1 to 10 carbon atoms and having one or more hydroxy groups.

Examples of such aliphatic hydroxycarboxylic acid include acyclic hydroxycarboxylic acids such as glycolic acid, lactic acid, tartronic acid, glyceric acid, hydroxybutyric acid (2-hydroxybutyric acid, 3-hydroxybutyric acid, γ-hydroxybutyric acid), malic acid, tartaric acid, citramalic acid, citric acid, isocitric acid, leucic acid, mevalonic acid, pantoic acid, pantothenic acid, and the like; and cyclic hydroxycarboxylic acids such as quinic acid, shikimic acid, and the like.

From the aspects of the effect of suppressing a decrease in the molecular weight of component (A) and the effect of improving the stability of component (A) and component (B) in a solution state, as component (C), an acyclic hydroxycarboxylic acid having 1 to 10 carbon atoms is preferred, acyclic hydroxycarboxylic acids having 2 to 6 carbon atoms such as glycolic acid, lactic acid, tartronic acid, glyceric acid, hydroxybutyric acid (2-hydroxybutyric acid, 3-hydroxybutyric acid, γ-hydroxybutyric acid), malic acid, tartaric acid, citramalic acid, citric acid, isocitric acid, leucic acid, mevalonic acid, pantoic acid, and the like are more preferred, and citric acid is particularly preferred.

As component (C), acyclic hydroxycarboxylic acid having 3 to 6 carbon atoms such as lactic acid, tartronic acid, glycerol acid, hydroxybutyric acid (2-hydroxybutyric acid, 3-hydroxybutyric acid, γ-hydroxybutyric acid), malic acid, tartaric acid, citramalic acid, citric acid, isocitric acid, leucine acid, mevalonic acid, pantoic acid, or the like is further preferred, acyclic hydroxycarboxylic acid having 4 to 6 carbon atoms and having two or more carboxyl groups such as malic acid, tartaric acid, citric acid, isocitric acid or the like is further more preferred, acyclic hydroxycarboxylic acid having 6 carbon atoms and having two or more carboxyl groups such as citric acid, isocitric acid or the like is even more preferred, and citric acid is particularly preferred.

In the present invention, a salt of the above-mentioned hydroxycarboxylic acid can also be used as component (C).

Such salt is not particularly limited as long as it is a pharmaceutically acceptable salt used for skin compositions. Examples thereof include salts with inorganic base such as alkali metal salts such as lithium salt, sodium salt, potassium salt, and the like; alkaline earth metal salts such as magnesium salt, calcium salt, and the like; ammonium salt, and the like, salts with organic base such as alkanol amine salts such as mono ethanolamine salt, diethanolamine salt, triethanolamine salt, and the like; salts with heterocyclic amine such as morpholine salt, piperidine salt, and the like; salts with basic amino acid such as arginine salt, lysine salt, histidine salt, and the like. An alkali metal salt such as sodium salt or the like is preferably used.

In the present invention, the above-mentioned aliphatic hydroxycarboxylic acid having 1 to 10 carbon atoms and a salt thereof to be used may be extracted and purified from animals and plants abundantly containing them, or obtained by chemical synthesis method, fermentation method, or gene recombinant method. Alternatively, commercially available products provided by each company may also be used.

In the composition for cosmetics of the present invention, one kind of the above-mentioned aliphatic hydroxycarboxylic acid having 1 to 10 carbon atoms and a salt thereof may be used alone, or two or more kinds thereof may be selected and used in combination.

The content ($W_C$) of component (C) in the composition for cosmetics of the present invention is preferably not less than 0.4 mass %, more preferably not less than 0.7 mass %. The content ($W_C$) of component (C) in the composition for cosmetics of the present invention is preferably not more than 12 mass %, more preferably not more than 7.5 mass %.

In another embodiment of the present invention, the content ($W_C$) of component (C) in the composition for cosmetics of the present invention is preferably not less than 0.4 mass %, more preferably not less than 0.7 mass %, further preferably not less than 1 mass %, further more preferably not less than 1.5 mass %, even more preferably not less than 1.7 mass %. In addition, the content ($W_C$) of component (C) in the composition for cosmetics of the present invention is preferably not more than 15 mass %, more preferably not more than 12 mass %, further preferably not more than 8 mass %, further more preferably not more than 5 mass %.

In still another embodiment of the present invention, the content ($W_C$) of component (C) in the composition for cosmetics of the present invention may be preferably 0.4 mass % to 15 mass %, more preferably 0.4 mass % to 12 mass %, further preferably 0.7 mass % to 12 mass %, further more preferably 0.7 mass % to 8 mass %, even more preferably 1 mass % to 8 mass %, still even more preferably 1 mass % to 5 mass %, particularly preferably 1.5 mass % to 5 mass % or 1.7 mass % to 5 mass %.

When a salt of aliphatic hydroxycarboxylic acid having 1 to 10 carbon atoms is contained as component (C), the above-mentioned content is shown as a content converted to that of a free form.

From the aspect of stability of the composition for cosmetics of the present invention, the ratio of content ($W_B$) of component (B) to the content ($W_A$) of component (A) ($W_B/W_A$) is preferably less than 2.4, more preferably not more than 2. The afore-mentioned ratio is preferably not less than 0.08, more preferably not less than 0.12.

In another embodiment of the present invention, the ratio of content ($W_B$) of component (B) to the content ($W_A$) of component (A) ($W_B/W_A$) is preferably less than 2.4, more preferably not more than 2, further preferably not more than 1. In addition, the aforementioned ratio is preferably not less than 0.08, more preferably not less than 0.12, further preferably not less than 0.36, further more preferably not less than 0.55.

In still another embodiment of the present invention, the ratio of content ($W_B$) of component (B) to the content ($W_A$) of component (A) ($W_B/W_A$) is preferably not less than 0.08 and less than 2.4, more preferably 0.08 to 2, further preferably 0.12 to 2, further more preferably 0.36 to 2, even more preferably 0.36 to 1, still even more preferably 0.55 to 1.

In addition, the ratio of content ($W_B$) of component (B) to the content ($W_C$) of component (C) ($W_B/W_C$) is preferably less than 3.3, more preferably not more than 3. The aforementioned ratio is preferably not less than 0.25, more preferably not less than 0.45.

In another embodiment of the present invention, the ratio of content ($W_B$) of component (B) to the content ($W_C$) of component (C) ($W_B/W_C$) is preferably not less than 0.25, more preferably not less than 0.45, further preferably not less than 1, further more preferably not less than 1.5.

In still another embodiment of the present invention, the ratio of content ($W_B$) of component (B) to the content ($W_C$) of component (C) ($W_B/W_C$) is preferably not less than 0.25 and less than 3.3, more preferably 0.45 to 3, further preferably 1 to 3, further more preferably 1.5 to 3.

The composition for cosmetics of the present invention may further contain pyrrolidonecarboxylic acid or an alkali metal salt thereof as a humectant for component (D), in addition to the above-mentioned components (A), (B) and (C).

In the present invention, any of the D-form, L-form, and DL-form of pyrrolidonecarboxylic acid can be used. L-form and DL-form are preferably used, and L-form is more preferably used.

As the alkali metal salt of pyrrolidonecarboxylic acid, lithium salt, sodium salt, potassium salt, and the like can be mentioned, and sodium salt is preferably used.

The pyrrolidonecarboxylic acid or an alkali metal salt thereof to be used can also be produced by chemical synthetic method, enzyme method, gene recombinant method, or the like. Alternatively, commercially available products provided by each company can also be used.

In the composition for cosmetics of the present invention, one kind of the above-mentioned pyrrolidonecarboxylic acid or a salt thereof may be used alone, or two or more kinds thereof may be selected and used in combination.

The content ($W_D$) of component (D) in the composition for cosmetics of the present invention is preferably not less than 1.5 mass %, more preferably not less than 2.5 mass %. The content ($W_D$) of component (D) in the composition for cosmetics composition of the present invention is preferably not more than 18 mass %, more preferably not more than 11 mass %.

In another embodiment of the present invention, the content ($W_D$) of component (D) in the composition for cosmetics of the present invention is preferably not less than 1.5 mass %, more preferably not less than 2.5 mass %, further preferably not less than 4 mass %. The content ($W_D$) of component (D) in the composition for cosmetics of the present invention is preferably not more than 18 mass %, more preferably not more than 15 mass %, further preferably not more than 12 mass %, still more preferably not more than 11 mass %.

In still another embodiment of the present invention, the content ($W_D$) of component (D) in the composition for cosmetics of the present invention may be preferably 1.5 mass % to 18 mass %, more preferably 2.5 mass % to 18 mass %, further preferably 2.5 mass % to 15 mass %, further more preferably 4 mass % to 15 mass %, still more preferably 4 mass % to 12 mass % or 4 mass % to 11 mass %.

When an alkali metal salt of pyrrolidonecarboxylic acid is contained as component (D), the above-mentioned content is shown as a content converted to that of a free form.

The composition for cosmetics of the present invention may further contain a skin conditioning agent arginine or a salt thereof as component (E), in addition to the above-mentioned components (A), (B), and (C).

Arginine (2-amino-5-guanidinopentanoic acid) is a naturally-occurring basic amino acid, and any of the D-form, L-form, and DL-form can be used. L-form and DL-form are preferably used, and L-form is more preferably used.

The salt of arginine is not particularly limited as long as it is a pharmaceutically acceptable salt and is used in a composition for skin. Examples thereof include acid addition salts and salts with bases.

Specifically, salts with inorganic bases, organic bases, inorganic acids, and organic acids, and salts with amino acids and the like can be mentioned.

Examples of the salts with inorganic bases include salts with alkali metals such as lithium, sodium, potassium, and the like, salts with alkaline earth metals such as magnesium, calcium, and the like, ammonium salts, and the like.

Examples of the salts with organic bases include salts with alkanol amines such as mono ethanolamine, diethanolamine, triethanolamine, and the like, salt with heterocyclic amines such as morpholine, piperidine, and the like, and the like.

Examples of the salts with inorganic acids include salts with hydrohalic acid (hydrochloric acid, hydrobromic acid, hydroiodic acid, etc.), sulfuric acid, nitric acid, phosphoric acid, and the like.

Examples of the salts with organic acids include salts with monocarboxylic acids such as formic acid, acetic acid, propanoic acid, and the like; salts with saturated dicarboxylic acids such as oxalic acid, malonic acid, succinic acid, and the like; salts with unsaturated dicarboxylic acids such as maleic acid, fumaric acid, and the like; salts with tricarboxylic acids such as aconitic acid and the like; salts with keto acids such as α-ketoglutaric acid and the like, and the like.

Examples of the salts with amino acids include salts with aliphatic amino acids such as alanine and the like; salts with aromatic amino acids such as tyrosine and the like; salts with basic amino acids such as lysine and the like; salts with acidic amino acids such as aspartic acid, glutamic acid, and the like; salts with lactam-forming amino acids such as pyroglutamic acid and the like, and the like.

The above-mentioned salts may be each a hydrate (hydrate salt), and examples of such hydrate include 1 hydrate to 6 hydrate.

In the present invention, arginine in a free form and hydrochloride are preferably used.

The above-mentioned arginine or a salt thereof may be all extracted and purified from naturally occurring animals and plants, or obtained by chemical synthesis method, fermentation method, enzyme method, or gene recombinant method.
Alternatively, commercially available products provided by each company may also be used.

In the composition for cosmetics of the present invention, one kind of the above-mentioned arginine or a salt thereof may be used alone, or two or more kinds thereof may be selected and used in combination.

The content ($W_E$) of component (E) in the composition for cosmetics of the present invention is preferably 1 mass % to 5 mass %.

When an arginine salt is contained as component (E), the above-mentioned content is shown as a content converted to that of a free form.

The composition for cosmetics of the present invention may further contain, in addition to the above-mentioned (A), (B), and component (C), one or more kinds selected from the group consisting of acidic amino acid and a salt thereof, basic amino acid other than arginine and a salt thereof, and neutral amino acid and a salt thereof, each of which can function as a humectant or a skin conditioning agent, as component (F).

Examples of the acidic amino acid include glutamic acid (2-aminopentanedioic acid), aspartic acid (2-aminobutanedioic acid) and the like.

Examples of the basic amino acid other than arginine include lysine (2,6-diamino hexanoic acid), histidine (2-amino-3-(1H-imidazol-4-yl)propionic acid), citrulline (2-amino-5-(carbamoylamino)pentanoic acid), ornithine (2,5-diamino pentanoic acid), and the like.

Examples of the neutral amino acid include glycine (aminoethane acid), alanine (2-aminopropionic acid), valine (2-amino-3-methylbutanoic acid), leucine (2-amino-4-methylpentanoic acid), and isoleucine (2-amino-3-methylpentanoic acid), each having an alkyl chain, serine (2-amino-3-hydroxypropanoic acid) and threonine (2-amino-3-hydroxybutanoic acid), each having a hydroxy group, cysteine (2-amino-3-sulfanylpropionic acid) and methionine (2-amino-4-(methylthio)butanoic acid), each including sulfur, asparagine (2-amino-3-carbamoylpropionic acid) and glutamine (2-amino-4-carbamoylbutanoic acid), each having an amide group, proline (pyrrolidine-2-carboxylic acid) having an imino group, phenylalanine (2-amino-3-phenylpropanoic acid), tyrosine (2-amino-3-(4-hydroxyphenyl) propanoic acid), and tryptophan (2-amino-3-(indolyl) propionic acid), each having an aromatic group, and the like.

As the above-mentioned amino acid other than glycine, any of the D-form, L-form, and DL-form can be used. L-form and DL-form are preferably used, and L-form is more preferably used.

The salts of the above-mentioned amino acids are not particularly limited as long as they are pharmaceutically acceptable salts and are used in skin compositions. They include acid addition salts, salts with bases, and hydrates, that are similar to those described above for (E) arginine.

In the present invention, the above-mentioned acidic amino acids are preferably used in the form of free forms and alkali metal salts such as sodium salt and potassium salt, the basic amino acids other than arginine are preferably used in the form of free forms and acid addition salts such as hydrochlorides, and neutral amino acids are preferably used in the form of free forms.

The above-mentioned acidic amino acids and salts thereof, basic amino acids other than arginine and salts thereof, and neutral amino acids and salts thereof to be used may be all extracted and purified from naturally occurring animals and plants, or obtained by chemical synthesis method, fermentation method, enzyme method, or gene recombinant method.
Alternatively, commercially available products provided by each company may also be used.

In the composition for cosmetics of the present invention, one kind may be selected from the group consisting of the above-mentioned acidic amino acid and a salt thereof, basic amino acid other than arginine and a salt thereof, and neutral amino acid and a salt thereof and used alone, or two or more kinds thereof may be selected and used in combination.

From the aspect of the effect of improving the moisture retaining property of the composition for cosmetics of the present invention, it is preferable to use two or more kinds selected from the group consisting of the above-mentioned amino acids and salts thereof, and more preferable to use one or more kinds selected from the group consisting of acidic amino acids and salts thereof, one or more kinds selected from the group consisting of basic amino acids other than arginine and salts thereof, and one or more kinds selected from the group consisting of neutral amino acids and salts thereof in combination.

Furthermore, in order to impart good moisture retaining property to the composition for cosmetics of the present invention, aspartic acid, glutamic acid, lysine, histidine, threonine, serine, proline, glycine, alanine, valine, leucine, phenylalanine, tyrosine, citrulline, and ornithine, that are amino acids constituting natural moisturizing factors, and salts of these are preferably used as component (F).

It is particularly preferable for the purpose of the present invention to use one or more kinds selected from the group consisting of glutamic acid and salts thereof, one or more kinds selected from the group consisting of lysine and salts thereof, and one or more kinds selected from the group consisting of serine and salts thereof in combination.

The content ($W_F$) of component (F) in the composition for cosmetics of the present invention is preferably 0.5 mass % to 3 mass % as the total content of component (F).

When a salt of acidic amino acid, basic amino acid other than arginine, or neutral amino acid is contained as component (F), the content of the salt is expressed in terms of the amount converted to a free form, and the above-mentioned content is calculated.

From the aspect of the effect of improving the moisture retaining property of the composition for cosmetics of the present invention, it is preferable to use the above-mentioned component (D) or component (F) in addition to components (A) to (C) in the composition for cosmetics of the present invention, and it is more preferable to use both component (D) and component (F).

From the aspect of the effect of improving the skin adhesion of the composition for cosmetics of the present invention, it is preferable to use the above-mentioned component (E) in addition to components (A) to (C) in the composition for cosmetics of the present invention.

In order to improve both the moisturizing effect and texture improvement effect of the composition for cosmetics of the present invention, it is particularly preferable to use the above-mentioned components (D), (E), and (F) in addition to components (A) to (C) in the composition for cosmetics composition.

The composition for cosmetics of the present invention is preferably adjusted to have pH 7 to 13, more preferably 7 to 11, further preferably 7.5 to 8.5. When the pH of the composition for cosmetics is within the aforementioned range, a decrease in the molecular weight of polyaspartic acid or a salt thereof as component (A) is suppressed well and the stability is improved.

In another embodiment of the present invention, the composition for cosmetics of the present invention is preferably adjusted to have pH 7 to 13, more preferably 7 to 11, further preferably 7.5 to 8.7, further more preferably 7.5 to 8.5.

The pH of the composition for cosmetics can be adjusted using pH adjusters generally used in cosmetics, such as hydrochloric acid, phosphoric acid, succinic acid, sodium hydroxide, potassium hydroxide, sodium acetate, sodium hydrogen phosphate, 1-amino-2-propanol and the like.

In the present invention, the pH of the composition for cosmetics is measured at 25° C. using a general glass electrode method.

The composition for cosmetics of the present invention can be obtained by adding the above-mentioned components (A) to (C), preferably further adding any one of or more of component (D), component (E), and component (F), adding as necessary pH adjuster and other general additives used in the field of preparations, and formulating into a liquid form such as solution, suspension, emulsified liquid, or the like; a semi-solid form such as gel, paste, cream, or the like; a solid form such as powder, granule, tablet, or the like; or the like according to formulation methods well known in the field of preparations, for example, the method described in the Japanese Pharmacopoeia, seventeenth Edition, General Rules for Preparation, [3] Monographs for Preparations, and the like.

Examples of the above-mentioned additive include excipient, binder, disintegrant, lubricant, coating agent, base, solvent, emulsifier, dispersing agent, suspending agent, stabilizer, thickening agent, antioxidant, antiseptic, preservative, flavor, colorant, and the like.

When the composition for cosmetics of the present invention is added to cosmetics, in order to perform the operation of adding and mixing the composition for cosmetics of the present invention conveniently and efficiently, it is preferable to make the composition for cosmetics of the present invention in a liquid form such as solution, suspension, emulsified liquid, or the like.

In this case, as general additives other than pH adjuster, solvents such as water, 1,3-butyleneglycol, glycerol, and the like; animal and plant fats and oils such as olive oil, soybean oil, camellia oil, sesame oil, peanuts oil, cacao butter, beef tallow, lard, and the like; waxes such as Carnauba wax, beeswax, jojoba oil, and the like; aliphatic alcohols such as octyldodecanol, cetanol, stearyl alcohol, and the like; fatty acids such as oleic acid, palmitic acid, stearic acid, and the like; oleaginous bases such as hydrocarbons (e.g., squalane, white petrolatum, liquid paraffin, ceresin, microcrystalline wax, and the like), suspending agents such as alginic acid propylene glycol ester, dioctyl sulfosuccinate sodium salt, soybean lecithin, povidone, and the like; surfactants or emulsifiers such as lecithin, hydrogenated lecithin, polyoxyethylene hydrogenated castor oil, polyoxyethylene alkylether(polyoxyethylene oleyl ether etc.), polyoxyethylene sorbitan fatty acid ester (polyoxyethylene sorbitan monolaurate, polyoxyethylene sorbitan monostearate, polyoxyethylene sorbitan monooleate, etc.), glyceryl fatty acid ester (glyceryl monostearate, etc.), fatty acid polyglyceryl ester (diglyceryldistearate, decaglyceryl isostearate, etc.), sucrose fatty acid ester, N-acylamino acid ester (N-myristoyl methylaminopropionic acid hexyldecyl, etc.), alkylsulfuric acid salt (sodium lauryl sulfate, etc.), and the like; thickening agents such as carboxyvinyl polymer, sodium polyacrylate, xanthan gum, carboxymethylcellulose, hydroxypropylcellulose, partially hydrolyzed polyvinyl alcohol, and the like; humectants such as trimethylglycine, maltitol and the like; stabilizers such as sodium edetate, polyoxyethylene polyoxypropylene glycol, and the like; antioxidants such as ascorbic acid, sodium erythorbate, tocopheryl acetate, dibutyl hydroxytoluene, and the like; preservatives such as sorbic acid, sodium dehydroacetate, methyl parahydroxybenzoate, propyl parahydroxybenzoate, butyl parahydroxybenzoate, phenoxyethanol and the like; dyes; pigments; flavors, and the like can be used as necessary.

From the aspects of improving the stability in a solution state of the composition for cosmetics of the present invention, or imparting the composition for cosmetics of the present invention with antibacterial property, the composition for cosmetics of the present invention preferably contains one or more kinds of polyhydric alcohol in addition to the above-mentioned components (A) to (C), or the above-mentioned components (A) to (C), and any one or more of the above-mentioned component (D), component (E), and component (F).

Examples of the polyhydric alcohol include propylene glycol, dipropylene glycol, glycerol, 1,3-butyleneglycol, 1,2-pentanediol (pentylene glycol), and the like. One kind may be used alone or two or more kinds thereof may be used in combination.

The content of polyhydric alcohol in the composition for cosmetics of the present invention is preferably 1 mass % to 50 mass %, more preferably 5 mass % to 20 mass %.

From the aspects of the stability in a solution state and antibacterial property of the composition for cosmetics of the present invention, other humectant with high water solubility, for example, trimethylglycine, urea, or the like, is preferably contained instead of the above-mentioned polyhydric alcohol, or together with the above-mentioned polyhydric alcohol.

The content of the above-mentioned other humectant in the composition for cosmetics of the present invention is preferably 1 mass % to 50 mass %, more preferably 1 mass % to mass %.

In addition, the composition for cosmetics of the present invention preferably contains water. As water, water suitable for production of cosmetics is used such as purified water such as distilled water, ion exchange water, and the like.

The content of water in the composition for cosmetics of the present invention is appropriately adjusted according to the preferable contents of other components. It is preferably not less than 10 mass %, more preferably not less than 20 mass %, further preferably not less than 30 mass %, further more preferably not less than 40 mass %, preferably not more than 95 mass %, more preferably not more than 93 mass %, further more preferably not more than 80 mass %, still even more preferably not more than 70 mass %.

One embodiment of the composition for cosmetics of the present invention may be a composition for cosmetics composed of the above-mentioned component (A), component (B), component (C), component (D), component (E), component (F), water, and as optional additives, one or more kinds selected from the group consisting of pH adjuster, excipient, binder, disintegrant, lubricant, coating agent, base, solvent, emulsifier, dispersing agent, suspending agent, stabilizer, thickening agent, antioxidant, antiseptic, preservative, flavor, colorant, and humectant.

Specifically, as one embodiment of the present invention, the composition for cosmetics of the present invention may be a composition for cosmetics composed only of (A) polyaspartic acid or a salt thereof,
(B) zinc pyrrolidonecarboxylate,
(C) aliphatic hydroxycarboxylic acid having 1 to 10 carbon atoms or a salt thereof,
(D) pyrrolidonecarboxylic acid or an alkali metal salt thereof,
(E) arginine or a salt thereof,
(F) one or more kinds selected from the group consisting of acidic amino acid and a salt thereof, basic amino acid other than arginine and a salt thereof, and neutral amino acid and a salt thereof,
(G) water, and
(H) as optional additives, one or more kinds selected from the group consisting of pH adjuster, excipient, binder, disintegrant, lubricant, coating agent, base, solvent, emulsifier, dispersing agent, suspending agent, stabilizer, thickening agent, antioxidant, antiseptic, preservative, flavor, colorant, and humectant.

More specifically, the composition for cosmetics of the present invention of the above-mentioned embodiment is composed only of component (A) 2.5 mass % to 13 mass %, component (B) 1 mass % to 12 mass %, component (C) 0.4 mass % to 12 mass %, component (D) 1.5 mass % to 18 mass %, component (E) 1 mass % to 5 mass %, component (F) 0.5 mass % to 3 mass %, component (G) 10 mass % to 93.1 mass %, and component (H) not more than 50 mass %, when the total amount is 100 mass %.

More preferred ranges of the contents of the components in the composition for cosmetics of the present invention of the above-mentioned embodiment are as described above.

Another embodiment of the composition for cosmetics of the present invention of the above-mentioned embodiment is composed only of component (A) 2 mass % to 20 mass %, component (B) 1 mass % to 15 mass %, component (C) 0.4 mass % to 15 mass %, component (D) 1.5 mass % to 18 mass %, component (E) 1 mass % to 5 mass %, component (F) 0.5 mass % to 3 mass %, component (G) 10 mass % to 93.6 mass %, and component (H) not more than 50 mass %, when the total amount is 100 mass %.

More preferred ranges of the contents of the components in the composition for cosmetics of the present invention of the above-mentioned another embodiment are as described above.

In the composition for cosmetics of the present invention, a decrease in the molecular weight of polyaspartic acid or a salt thereof is suppressed, and the stability of polyaspartic acid or a salt thereof and zinc pyrrolidonecarboxylate in a solution state is improved.

Therefore, the composition for cosmetics of the present invention can stably contain polyaspartic acid or a salt thereof having superior moisturizing effect, improved adhesion to the skin, and good dispersing ability of powder such as pigment, etc., and zinc pyrrolidonecarboxylate having various physiological functions such as sebum suppressive effect, antibacterial action, skin astringent effect, antiaging effect, and the like.

Therefore, the composition for cosmetics of the present invention is preferably used for stably blending polyaspartic acid or a salt thereof with zinc pyrrolidonecarboxylate to produce various cosmetics.

Examples of the cosmetics in which the composition for cosmetics of the present invention can be blended include skin cosmetics such as skin lotion, milky lotion, serum, gel, oil-in-water type or water-in-oil type cream, facial mask, and the like; cleansing cosmetics such as facial cleansing cream, cleansing cream, cleansing lotion, and the like; foundation primers such as make up base lotion, makeup base cream, and the like; makeup cosmetics such as foundation, eye color, blush, eyeliner, mascara, lip rouge and the like; hair cosmetics such as shampoo, conditioner, hair tonic, hair cream, and the like; body cosmetics such as body soap, body lotion, body cream, and the like; suntan cosmetics such as tanning lotion and the like; sunscreen cosmetics such as sunscreen lotion, sunscreen cream, and the like, and the like.

The composition for cosmetics of the present invention can also stably blend polyaspartic acid or a salt thereof in emulsion cosmetics. Thus, the composition for cosmetics of the present invention can be preferably used for skin cosmetics, foundation primers, makeup cosmetics, suntan cosmetics, sunscreen cosmetics, and the like that are in an emulsified liquid state or a cream form.

In addition, the composition for cosmetics of the present invention can achieve good demonstration of adhesion of polyaspartic acid or a salt thereof to the skin and powder dispersing ability of pigment and the like. Thus, the composition for cosmetics of the present invention can be more preferably used for foundation primers, makeup cosmetics, sunscreen cosmetics, and the like containing powders such as pigment and the like.

Therefore, the composition for cosmetics of the present invention can be particularly preferably used for emulsified cosmetics containing powders such as pigment and the like such as foundation primers, makeup cosmetics, sunscreen cosmetics, and the like in the form of emulsified liquid or cream.

Therefore, the present invention provides cosmetics containing the above-mentioned composition for cosmetics of the present invention, particularly preferably provides cosmetics containing the above-mentioned composition for cosmetics of the present invention and a powder.

Examples of the powder include oxides such as yellow iron oxide, red iron oxide, black iron oxide, fine-grained iron oxide, zirconium oxide, magnesium oxide, chrome oxide, cobalt oxide, zinc oxide, fine-grained zinc oxide, titanium oxide, fine-grained titanium oxide, alumina, cerium oxide, and the like; silicates such as silica, porous silica, aluminum silicate, magnesium silicate, silicon carbide, sericite, mica, talc, kaolin, clay, bentonite, and the like; sulfates such as calcium sulfate, barium sulfate, plate-like barium sulfate, butterfly-shaped barium sulfate, magnesium sulfate, and the like; carbonates such as calcium carbonate, magnesium carbonate, and the like; carbons such as carbon black and the like; white pigments other than the aforementioned white pigments (e.g., oxychloride bismuth, boron nitride, hydroxyapatite, and the like); blue pigments such as ultramarine blue, iron blue, and the like; tar pigments, lake pigments, and the like. One kind of these powders may be used alone or two or more kinds thereof may be used in combination.

In addition, the powder to be contained in cosmetics together with the composition for cosmetics of the present invention may be a complex of those mentioned above (e.g., silica-coated titanium oxide, mica-coated titanium oxide, titanium-coated mica, etc.), or may be one obtained by a surface treatment, such as silicone treatment, fluorine compound treatment, silane coupling agent treatment, silane treatment, organic titanate treatment, acylated fatty acid treatment (e.g., stearoylglutamic acid treatment), metal soap treatment (e.g., aluminum stearate treatment), oleum treatment, amino acid treatment, and the like, of the above-mentioned powders, for example, silicone-treated talc, silicone-treated mica, silicone-treated sericite, silicone treated titanium oxide, silicone treated red iron oxide, silicone-treated yellow iron oxide, silicone-treated black iron oxide, stearoylglutamic acid-treated titanium oxide, stearoylglutamic acid-treated yellow iron oxide, stearoylglutamic acid-treated red iron oxide, stearoylglutamic acid-treated black iron oxide, aluminum stearate-treated titanium oxide, and the like.

Other features of the invention will become apparent in the course of the following descriptions of exemplary embodiments which are given for illustration of the invention and are not intended to be limiting thereof.

EXAMPLES

Examples 1 to 3, Comparative Example 1. Composition for Cosmetics

According to the formulations shown in Table 1, components (A) to (C) were sequentially added to purified water and mixed uniformly, and the pH was adjusted using a pH adjuster to prepare liquid composition for cosmetics of Examples 1 to 3 and Comparative Example 1. The pH in the table indicates the value measured by the glass electrode method at 25° C.

As component (A), "AQUADEW SPA-30B" (weight average molecular weight=3,000 to 5,000) (Ajinomoto Co., Inc.) was used. The content of component (A) in the table shows the net content of sodium polyaspartate. As component (B) and component (C), commercially available products for cosmetics were used. As the pH adjuster, sodium hydroxide (commercially available product for cosmetics) was used.

1,3-Butyleneglycol and disodium ethylenediaminetetraacetate in the table are components derived from "AQUADEW SPA-30B" (Ajinomoto Co., Inc.).

For component (A) and component (C), the content converted to that of a free form thereof is shown in parentheses. The ratio of content ($W_B$) of component (B) to the content ($W_A$) of component (A) ($W_B/W_A$) and the ratio of content ($W_B$) of component (B) to the content ($W_C$) of component (C) ($W_B/W_C$) are values calculated using, as the content of component (A) and the content of component (C), the contents converted to those of free forms thereof.

For each composition for cosmetics of Examples 1 to 3 and Comparative Example 1, the stability in a solution state and stability of sodium polyaspartate were evaluated as shown below. The evaluation results are also shown in Table 1.

(1) Stability in a Solution State

Immediately after preparing each composition for cosmetics, the state was observed at ordinary temperature (25° C.), and then the compositions were respectively stored at 50° C. for 1 month and at 70° C. for 9 days, and the state after storage was observed. The stability in a solution state was evaluated according to the following evaluation criteria.

Evaluation Criteria

⊙; No deposition or precipitation of the contained components was observed even in a severe acceleration test (storage at 70° C. for 9 days).

○; No deposition or precipitation of the contained components was observed immediately after preparation or in an accelerated test (storage at 50° C. for 1 month), but deposition or precipitation of the contained components was observed in a severe acceleration test (storage at 70° C. for 9 days).

Δ; No deposition or precipitation of the contained components was observed immediately after preparation but deposition or precipitation of the contained components was observed in an acceleration test (storage at 50° C. for 1 month).

x; Deposition or precipitation of the contained components was observed immediately after preparation.

(2) Stability of Sodium Polyaspartate

Each composition for cosmetics of Examples 1 to 3 and Comparative Example 1 were stored at 70° C. for 9 days, the weight average molecular weight of sodium polyaspartate in each composition was measured by gel filtration chromatography, and the stability of sodium polyaspartate was evaluated according to the following evaluation criteria.

Evaluation Criteria

⊙; The weight average molecular weight of sodium polyaspartate is not less than 2,400.

○; The weight average molecular weight of sodium polyaspartate is not less than 2,000 and less than 2,400.

Δ; The weight average molecular weight of sodium polyaspartate is not less than 1,600 and less than 2,000.

x; The weight average molecular weight of sodium polyaspartate is less than 1,600.

TABLE 1

| component/ evaluation item | Example 1 | Example 2 | Example 3 | Comparative Example 1 |
|---|---|---|---|---|
| (A) sodium polyaspartate | 15.0 (12.6) | 10.0 (8.4) | 10.0 (8.4) | 10.0 (8.4) |
| (B) zinc pyrrolidone-carboxylate | 5.0 | 5.0 | 5.0 | 5.0 |
| (C) sodium citrate | 2.5 (1.9) | 10.0 (7.4) | 2.5 (1.9) | 0 |
| 1,3-butyleneglycol | 4.0 | 2.7 | 2.7 | 2.7 |
| disodium ethylenediamine-tetraacetate | 0.05 | 0.03 | 0.03 | 0.03 |
| purified water | rest | rest | rest | rest |
| pH adjuster | q.s. | q. s. | q.s. | q.s. |
| total | 100 | 100 | 100 | 100 |
| pH | 8.5 | 8.5 | 7.0 | 8.5 |
| $W_B/W_A$ | 0.4 | 0.6 | 0.6 | 0.6 |
| $W_B/W_C$ | 2.6 | 0.7 | 2.6 | — |
| stability in solution state | ⊙ | ⊙ | ⊙ | x |
| stability of sodium polyaspartate | Δ | Δ | Δ | Not performed |

* Numerical value corresponding to each component in table is the content (mass %) of each, and the numerical value in parentheses is a content (mass %) converted to that of a free form thereof.

As shown in Table 1, the composition for cosmetics of Comparative Example 1 not containing component (C) could not sufficiently dissolve component (A) and component (B).

On the other hand, in the compositions for cosmetics of Examples 1 to 3 containing component (C) in addition to components (A) and (B), a slight decrease in the molecular weight of sodium polyaspartate was observed in a severe acceleration test (storage at 70° C. for 9 days) but deposition or precipitation of the contained components was not observed, and good stability in a solution state was observed.

Examples 4 to 23. Composition for Cosmetics

According to the formulation shown in Table 2, components (A) to (D) were sequentially added to purified water and mixed uniformly, and the pH was adjusted using a pH adjuster to prepare liquid compositions for cosmetics of Examples 4 to 23. The pH in the table indicates the value measured by the glass electrode method at 25° C.

The component (A) to component (C) and pH adjuster used were the same as those used in the preparation of the above-mentioned Examples 1 to 3. As component (D), a commercially available product for cosmetics was used.

The content of component (A) in the table shows the net content of sodium polyaspartate, and 1,3-butyleneglycol and disodium ethylenediaminetetraacetate are components derived from "AQUADEW SPA-30B" (Ajinomoto Co., Inc.).

For component (A), component (C), and component (D), the content converted to that of a free form thereof is shown in parentheses. The ratio of content ($W_B$) of component (B) to the content ($W_A$) of component (A) ($W_B/W_A$) and the ratio of content ($W_B$) of component (B) to the content ($W_C$) of component (C) ($W_B/W_C$) are values calculated using, as the content of component (A) and the content of component (C), the contents converted to those of free forms thereof.

The compositions for cosmetics of Examples 4 to 23 were evaluated for the stability in a solution state and stability of sodium polyaspartate in the same manner as in the respective compositions for cosmetics of the above-mentioned Examples 1 to 3 and Comparative Example 1. The evaluation results are also shown in Table 2.

TABLE 2

| component/ evaluation item | Ex. 4 | Ex. 5 | Ex. 6 | Ex. 7 | Ex. 8 | Ex. 9 | Ex. 10 | Ex. 11 | Ex. 12 | Ex. 13 | Ex. 14 | Ex. 15 | Ex. 16 | Ex. 17 | Ex. 18 | Ex. 19 | Ex. 20 | Ex. 21 | Ex. 22 | Ex. 23 |
|---|---|---|---|---|---|---|---|---|---|---|---|---|---|---|---|---|---|---|---|---|
| (A) sodium poly-aspartate | 10.0 (8.4) | 10.0 (8.4) | 15.0 (12.6) | 10.0 (8.4) | 10.0 (8.4) | 10.0 (8.4) | 3.0 (2.5) | 10.0 (8.4) | 10.0 (8.4) | 4.0 (3.4) | 5.0 (4.2 | 10.0 (8.4) | 10.0 (8.4) | 10.0 (8.4) | 10.0 (8.4) | 10.0 (8.4) | 10.0 (8.4) | 10.0 (8.4) | 10.0 (8.4) | 10.0 (8.4) |
| (B) zinc pyrrolidone-carboxylate | 5.0 | 5.0 | 5.0 | 1.0 | 12.0 | 5.0 | 5.0 | 4.5 | 5.0 | 5.0 | 5.0 | 3.0 | 3.0 | 5.0 | 7.0 | 10.0 | 5.0 | 5.0 | 5.0 | 5.0 |
| (C) sodium citrate | 2.5 (1.9) | 2.5 (1.9) | 2.5 (1.9) | 1.0 (0.7) | 6.0 (4.4) | 15.0 (11.2) | 7.0 (5.2) | 2.0 (1.5) | 2.5 (1.9) | 5.0 (3.7) | 2.5 (1.9) | 1.5 (1.1) | 3.0 (2.2) | 10.0 (7.4) | 5.0 (3.7) | 5.0 (3.7) | 10.0 (7.4) | 10.0 (7.4) | 10.0 (7.4) | 10.0 (7.4) |
| (D) sodium pyrrolidone-carboxylate | 12.0 (10.3) | 5.0 (4.3) | 5.0 (4.3) | 5.0 (4.3) | 5.0 (4.3) | 5.0 (4.3) | 5.0 (4.3) | 5.0 (4.3) | 5.0 (4.3) | 5.0 (4.3) | 5.0 (4.3 | 5.0 (4.3) | 5.0 (4.3) | 5.0 (4.3) | 5.0 (4.3) | 5.0 (4.3 | 5.0 (4.3) | 5.0 (4.3) | 5.0 (4.3) | 5.0 (4.3) |
| 1,3-butylene glycol- | 2.7 | 2.7 | 4.0 | 2.7 | 2.7 | 2.7 | 0.8 | 2.7 | 2.7 | 1.1 | 1.3 | 2.7 | 2.7 | 2.7 | 2.7 | 2.7 | 2.7 | 2.7 | 2.7 | 2.7 |
| disodium ethylene-diamine-tetraacetate | 0.03 | 0.03 | 0.05 | 0.03 | 0.03 | 0.03 | 0.0 | 0.03 | 0.03 | 0.01 | 0.02 | 0.03 | 0.03 | 0.03 | 0.03 | 0.03 | 0.03 | 0.03 | 0.03 | 0.03 |
| purified water | rest | rest | rest | rest | rest | rest | rest | rest | rest | rest | rest | rest | rest | rest | rest | rest | rest | rest | rest | rest |
| pH adjuster | q.s. | q.s. | q.s. | q.s. | q.s. | q.s. | q.s. | q.s. | q.s. | q.s. | q.s. | q.s. | q.s. | q.s. | q.s. | q.s. | q.s. | q.s. | q.s. | q.s. |
| total | 100 | 100 | 100 | 100 | 100 | 100 | 100 | 100 | 100 | 100 | 100 | 100 | 100 | 100 | 100 | 100 | 100 | 100 | 100 | 100 |
| pH | 8.5 | 8.5 | 8.5 | 8.5 | 8.5 | 8.5 | 8.5 | 8.5 | 7.5 | 8.5 | 8.5 | 8.5 | 8.5 | 8.5 | 8.5 | 8.5 | 7.0 | 9.0 | 10.0 | 11.0 |
| $W_B/W_A$ | 0.60 | 0.60 | 0.40 | 0.12 | 1.40 | 0.60 | 2.00 | 0.54 | 0.60 | 1.47 | 1.19 | 0.36 | 0.36 | 0.60 | 0.83 | 1.19 | 0.60 | 0.60 | 0.60 | 0.60 |
| $W_B/W_C$ | 2.63 | 2.63 | 2.63 | 1.43 | 2.73 | 0.45 | 0.96 | 3.00 | 2.63 | 1.35 | 2.63 | 2.73 | 1.34 | 0.68 | 1.89 | 2.70 | 0.68 | 0.68 | 0.68 | 0.68 |
| stability in solution state | ◎ | ◎ | ◎ | Δ | Δ | ◎ | ◎ | Δ | ◎ | ◎ | ○ | ◎ | ◎ | ◎ | ◎ | Δ | ◎ | ◎ | ◎ | ◎ |
| stability of sodium poly-aspartate | ◎ | ◎ | ◎ | ○ | ○ | ○ | ○ | ○ | ○ | ○ | ◎ | ○ | ○ | ◎ | ○ | ◎ | Δ | Δ | Δ | Δ |

* Numerical value corresponding to each component in table is the content (mass %) of each, and the numerical value in parentheses is a content (mass %) converted to that of a free form thereof.

As shown in Table 2, the compositions for cosmetics of Examples 4 to 19 containing components (A) to (D) and having pH 7.5 or 8.5 scarcely showed or slightly showed a decrease in the molecular weight of sodium polyaspartate even in a severe acceleration test.

The respective composition for cosmetics of Examples 20 to 23 having the same contents of components (A) to (D) with the composition for cosmetics of Example 17 but respectively having pHs 7.0, 9.0, 10.0, and 11.0 showed a slight decrease in the molecular weight of sodium polyaspartate in a severe acceleration test, but showed no decrease in the molecular weight that poses problems in providing them as products.

The composition for cosmetics of Example 7 in which the ratio of the content of component (B) to the content of component (A) ($W_B/W_A$) is 0.12, and compositions for cosmetics of Examples 8, 11, and 19 in which the ratio of the content of component (B) to the content of component (C) ($W_B/W_C$) is 2.73, 3.00, and 2.70, respectively, showed deposition or precipitation of the contained components in an acceleration test, but other compositions for cosmetics showed good stability in a solution state.

From the above-mentioned results, it was suggested that the stability in a solution state becomes good when the ratio of the content of component (B) to the content of component (A) ($W_B/W_A$) is not less than 0.12 and the ratio of the content of component (B) to the content of component (C) ($W_B/W_C$) is not more than 3.

In addition, it was suggested that a decrease in the molecular weight of component (A) is suppressed well when the pH of the composition for cosmetics is adjusted to 7 to 11, and a decrease in the molecular weight of component (A) is suppressed better when adjusted to 7.5 to 8.5.

Example 24. Composition for Cosmetics

According to the formulations shown in Table 3, components (A) to (F) and other components were sequentially added to purified water and mixed uniformly to prepare a composition for cosmetics of Example 24. The components (A) to (D) used were the same as those used in the above-mentioned Examples 1 to 23, and component (E), component (F), and other components used were commercially available products for cosmetics.

The content of component (A) in the table shows the net content of sodium polyaspartate, and the content of 1,3-butyleneglycol includes the content of 1,3-butyleneglycol derived from “AQUADEW SPA-30B” (Ajinomoto Co., Inc.). In addition, disodium ethylenediaminetetraacetate contained therein is a component derived from “AQUADEW SPA-30B” (Ajinomoto Co., Inc.).

For component (A), component (C), component (D), and component (F) in a salt form, the content converted to that of a free form thereof is shown in parentheses.

The pH of the composition for cosmetics of Example 24 was measured by the glass electrode method at 25° C. and was found to be 8.5.

The composition for cosmetics of Example 24 was evaluated for the stability in a solution state and stability of sodium polyaspartate in the same manner as in the above-mentioned Examples 1 to 3 and Comparative Example 1 and was found to be good in both.

In addition, the composition for cosmetics of Example 24 containing 1,3-butylene glycol and trimethylglycine in addition to components (A) to (F) showed good antibacterial property even though it did not contain a preservative.

Furthermore, in the composition for cosmetics of Example 24, better skin adhesion feeling and better moist feeling were observed as compared with the composition for cosmetics of Example 1.

TABLE 3

| | component | Example 24 |
|---|---|---|
| (A) | sodium polyaspartate | 10(8.4) |
| (B) | zinc pyrrolidonecarboxylate | 5.0 |
| (C) | sodium citrate | 2.5(1.9) |
| (D) | sodium pyrrolidonecarboxylate | 12.0(10.3) |
| (E) | arginine | 2.0 |
| (F) | glutamic acid | 0.09 |
| | lysine hydrochloride | 0.14(0.11) |
| | serine | 0.77 |
| others | trimethylglycine | 7.50 |
| | 1,3-butyleneglycol | 10 |
| | disodium ethylenediaminetetraacetate | 0.03 |
| pH adjuster | sodium hydroxide | 0.46 |
| | purified water | rest |
| total | | 100 |

* Numerical value corresponding to each component in table is the content (mass %) of each, and the numerical value in parentheses is a content (mass %) converted to that of a free form thereof.

Therefore, it was suggested in the composition for cosmetics of the present invention that the moist feeling is enhanced by using component (D) and component (F) in addition to components (A) to (C), and the skin adhesion feeling is enhanced by using component (E).

It was also suggested that antibacterial property can be imparted to compositions for cosmetics without impairing the stability thereof in a solution state, by using polyhydric alcohol or trimethylglycine.

INDUSTRIAL APPLICABILITY

As described in detail above, the present invention can provide a composition for cosmetics, containing polyaspartic acid or a salt thereof and zinc pyrrolidonecarboxylate, in which a decrease in the molecular weight of polyaspartic acid or a salt thereof is suppressed, and further, the stability of polyaspartic acid or a salt thereof and zinc pyrrolidonecarboxylate in a solution state is improved.

The composition for cosmetics of the present invention is useful as a premixed composition for cosmetics that can be stably and conveniently blended in cosmetics, and can impart the cosmetics with high moisture retaining property and good skin adhesion, as well as sebum suppressive effect, antibacterial action, skin astringent effect, antiaging effect, and the like.

Where a numerical limit or range is stated herein, the endpoints are included. Also, all values and subranges within a numerical limit or range are specifically included as if explicitly written out.

As used herein the words “a” and “an” and the like carry the meaning of “one or more.”

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A composition for cosmetics, comprising:

(A) at least one polyaspartic acid or a salt thereof;

(B) zinc pyrrolidonecarboxylate; and (C) at least one aliphatic hydroxycarboxylic acid having 1 to 10 carbon atoms or a salt thereof, wherein a content of the (A) at least one polyaspartic acid or a salt thereof is 2.5 mass % to 13 mass % as a content converted to that of a free form thereof, based on the total mass of the composition, a content of the (B) zinc pyrrolidonecarboxylate is 1 mass % to 12 mass %, based on the total mass of the composition, a ratio of a content of component (B) ($W_B$) to a content of component (A) ($W_A$) ($W_B/W_A$) is 0.12 to 2, and a ratio of a content of component (B) (Wp) to a content of component (C) ($W_C$) ($W_B/W_C$) is 0.45 to 3.

2. The composition according to claim 1, wherein the (C) at least one aliphatic hydroxycarboxylic acid having 1 to 10 carbon atoms or a salt thereof is an acyclic hydroxycarboxylic acid having 2 to 6 carbon atoms or a salt thereof.

3. The composition according to claim 1, further comprising (D) pyrrolidonecarboxylic acid or an alkali metal salt thereof.

4. The composition according to claim 1, further comprising (E) arginine or a salt thereof.

5. The composition according to claim 1, further comprising (F) one or more selected from the group consisting of an acidic amino acid and a salt thereof, a basic amino acid other than arginine and a salt thereof, and a neutral amino acid and a salt thereof.

6. The composition according to claim 1, further comprising one or more polyhydric alcohol.

7. The composition according to claim 1, further comprising trimethylglycine.

8. The composition according to claim 1, wherein the composition has a pH of 7 to 13 at 25° C.

9. A cosmetic comprising the composition according to claim 1 and a powder.

10. A cosmetic comprising the composition according to claim 1.

* * * * *